United States Patent [19]

Van Meter

[11] Patent Number: 5,517,850

[45] Date of Patent: May 21, 1996

[54] ROTOR-STATOR ADAPTERS WITH INTERNALLY THREADED STATOR COLLAR EXTERNALLY THREADED NUT FOR SENSITIVE ROTATING VISCOMETERS

[75] Inventor: John L. Van Meter, Midland, Mich.

[73] Assignee: Tannas Co., Midland, Mich.

[21] Appl. No.: 336,379

[22] Filed: Nov. 8, 1994

Related U.S. Application Data

[63] Continuation-in-part of Ser. No. 308,918, Sep. 20, 1994.

[51] Int. Cl.$^6$ ............................ F16B 39/28; F16B 2/06; G01N 11/14
[52] U.S. Cl. .................. 73/54.35; 73/54.21; 464/79; 464/78; 411/305; 411/395; 411/418
[58] Field of Search ................. 73/54.35, 54.21, 73/54.28, 54.31, 54.33; 464/80, 79, 78; 411/305, 306, 395, 418

[56] References Cited

U.S. PATENT DOCUMENTS

| | | | |
|---|---|---|---|
| Re. 20,542 | 10/1937 | Dyer | 151/21 |
| 122,426 | 1/1872 | Andrew | 403/314 |
| 453,622 | 6/1891 | Cheney | 403/290 X |
| 668,017 | 2/1901 | Pessano | 403/308 |
| 724,475 | 4/1903 | Hilmo | 403/290 X |
| 817,588 | 4/1906 | Reising | 403/310 |
| 904,341 | 11/1908 | Lindstrom . | |
| 1,251,464 | 1/1918 | Becker . | |
| 1,321,264 | 11/1919 | Wagner et al. | 403/300 |
| 2,034,658 | 3/1936 | Jones et al. | 265/11 |
| 2,047,219 | 7/1936 | Meyer et al. | 188/74 |
| 2,056,248 | 10/1936 | Buchanan | 173/303 |
| 2,160,694 | 5/1939 | Buchanan | 287/75 |
| 3,359,528 | 12/1967 | Scholz | 339/65 |
| 3,492,908 | 2/1970 | Thurston | 85/47 |
| 3,518,748 | 7/1970 | Howlett | 29/452 |
| 3,677,070 | 7/1972 | Norcross | 73/57 |
| 3,810,078 | 5/1974 | Chordas | 339/268 R |
| 3,935,729 | 2/1976 | McCarthy | 73/60 |
| 4,214,475 | 7/1980 | Carter et al. | 73/59 |
| 4,441,837 | 4/1984 | Mastroni | 403/300 |
| 4,524,484 | 6/1985 | Graham | 16/115 |
| 4,623,277 | 11/1986 | Wayne et al. | 403/314 |
| 4,645,473 | 2/1987 | Mochizuki | 464/79 |
| 4,648,263 | 3/1987 | Deysarkar et al. | 73/59 |
| 5,004,367 | 4/1991 | Wood, Jr. | 403/36 |
| 5,177,997 | 1/1993 | Maciejewski | 73/54.24 |
| 5,369,988 | 12/1994 | Selby | 73/54.28 |

FOREIGN PATENT DOCUMENTS

| | | | |
|---|---|---|---|
| 0821495 | 12/1937 | France | 411/418 |
| 1127593 | 9/1968 | United Kingdom | 411/306 |

OTHER PUBLICATIONS

Serial No. 08/308918 Filed Sep. 20, 1994, "Rotor–Stator Adapter for Sensitive Rotating Instruments." ASTM D 5133–90 (1990).

*Primary Examiner*—Hezron E. Williams
*Assistant Examiner*—J. David Wiggins
*Attorney, Agent, or Firm*—Christopher J. Rudy

[57] ABSTRACT

Sensitive rotating viscometers which include a head, rotor and stator, for example, a Brookfield viscometer, and have their head supported by a hollow housing and their stator held in place by the same hollow housing are improved by an internally threaded wall in a lower portion of the hollow support member, having means to exert guiding pressure on a means to accept pressure of a correspondingly, externally threaded nut, the correspondingly, externally threaded nut for attachment within the internally threaded wall, which threaded nut has an extension which is perforately slotted, the nut extension having the means to accept pressure, so as to cause the nut extension to be directed inwardly by tightening of the nut within the internally threaded wall, so as to cause snug contact between the lower interior surface of the hollow support member and the exterior cylindrical surface of the stator. The device may be embodied as a separable collar housing and stator/tube collar with such an aforesaid nut.

11 Claims, 1 Drawing Sheet

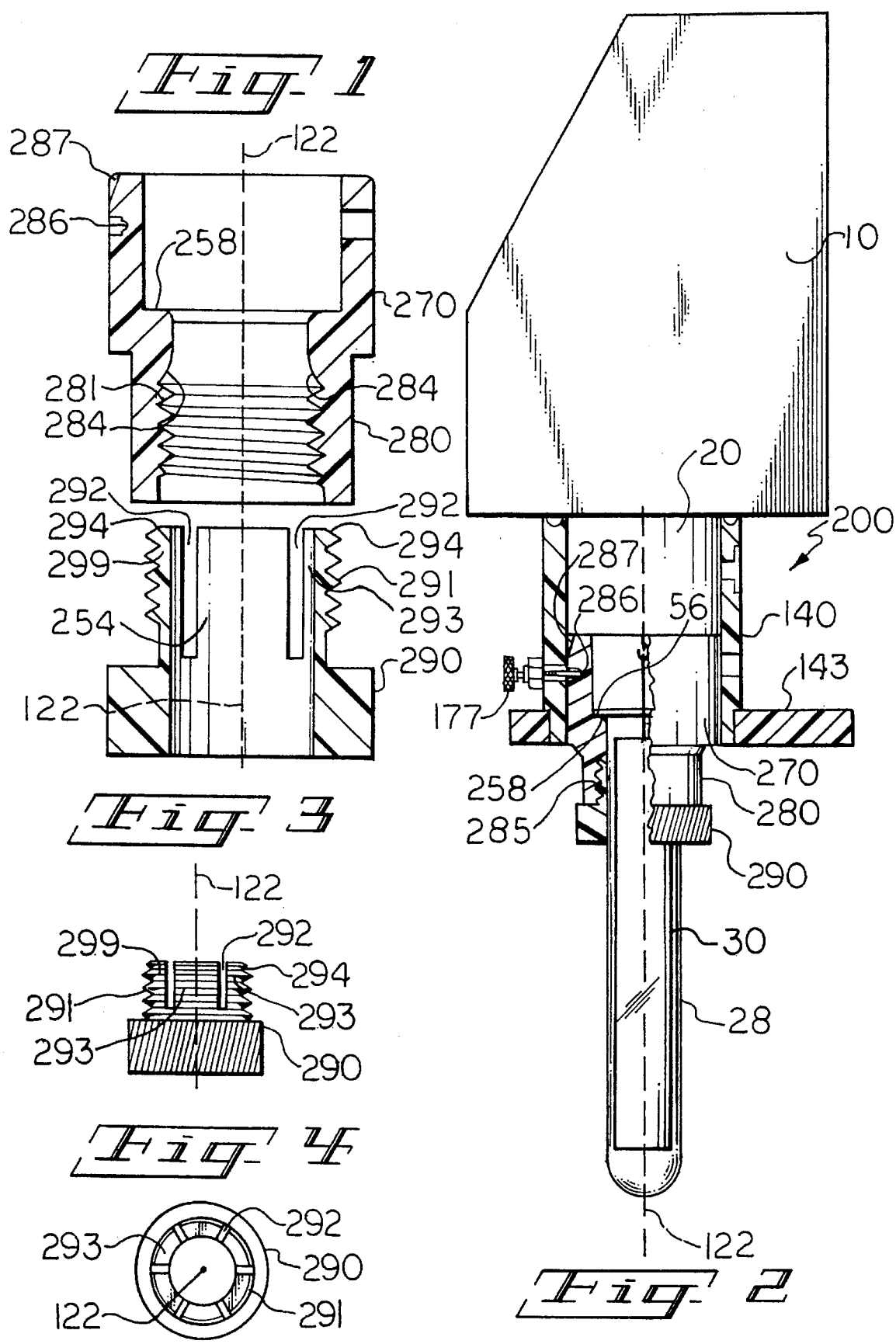

5,517,850

ROTOR-STATOR ADAPTERS WITH INTERNALLY THREADED STATOR COLLAR EXTERNALLY THREADED NUT FOR SENSITIVE ROTATING VISCOMETERS

CROSS-REFERENCE AND INCORPORATIONS BY REFERENCE

This is a continuation-in-part of application Ser. No. 08/308,918 filed on Sep. 20, 1994, incorporated herein by reference. Also incorporated herein by reference are U.S. Pat. No. 4,648,263 and ASTM D 5133 (1990).

FIELD

In general, the present invention concerns rotating viscometers, useful in measuring viscosities of liquids. More particularly, it concerns attachments for centering and supporting various rotational and static parts of the viscometer.

BACKGROUND

As described in the parent hereto, rotational viscometers require a rotating element called the rotor and a stationary element in fluid contact with the rotor which is called the stator. Usually, particularly in sensitive rotational viscometers such as the Brookfield viscometer, the rotor, which is driven by the Brookfield head, is immersed in a large container of liquid. In some applications such as in the well-known Scanning Brookfield Technique, developed by Mr. Theodore W. Selby and licensed to the Tannas Co., Midland, Mich., used in ASTM D 5133, and improved by a support and centering device disclosed by Deysarkar et al., U.S. Pat. 4,648,263, and in the parent hereto, the rotor must be relatively close to the stator wall to gain the necessary sensitivity. In such a case, the rotor must be centered very carefully.

In practice, problems are encountered with the commercially available support and centering attachment of Deysarkar et al., which is known commercially as the Pennzoil/ Tannas rotor/stator centering adapter, Tannas Model SBV-P. In particular, and in reference to the foregoing patent, an O-ring, present in the SBV-P adapter in a slot cut in interior surface 54 of cylindrical member 70, can swell as from contact with solvents or oil to the point where sometimes, upon the contraction of the constraining cylindrical member 70, a glass stator 28 may break. The O-ring also may become worn or oily, and, if a loose fit between cylindrical member 70 and stator 28 is engendered, slippage and rotation of the stator occurs during testing, which destroys the value of the test. Furthermore, the O-ring can be difficult to install and remove for replacement. Another effect of low-temperature contraction of cylindrical member 70 is that, when bath 44 controls the test liquid temperature at minus 40 degrees C., or below, separation of parts of device 40, to include removal of a glass stator 28 filled with tested liquid from the lower end 52 of the device, becomes very difficult because of the aforementioned contraction of the engineering thermoplastic employed to make the adapter. Other problems exist, in particular with the device disclosed by Deysarkar et al.

What is needed is another adapter which overcomes such problems while providing for precise centering of the rotor spindle in the stator of a sensitive rotating viscometer. The adapter should be readily manufacturable—and be efficient to operate, especially by even inexperienced operators.

SUMMARY

The present invention provides for, especially in a device for supporting a sensitive viscometer above a cylindrical stator containing a predetermined quantity of fluid, the fluid having a viscosity, the viscosity of the fluid being measured by a viscometer with a cylindrical rotor suspended from a pivot housing fixed to a lower end of the viscometer and centered within the fluid by the device, the rotor being rotatable about its longitudinal axis by the viscometer motar and cooperating with the stator and fluid to create drag related to the viscosity, the device having a hollow support member having an open upper end and upper interior surface shaped to correspond and snugly engage an exterior surface of the pivot housing, the viscometer projecting upwardly from substantially an upper end of the support member, first means for retaining the pivot housing in stationary position and snug contact with the upper interior surface, the support member further including a lower interior cylindrical surface in snug contact with an exterior cylindrical surface of the stator, and second means for retaining the stator in stationary position and snug contact with the lower cylindrical surface, the upper and lower surfaces being coaxial with each other to substantially precisely center the rotor within the stator, an improvement which comprises:

an internally threaded wall in a lower portion of the support member, having means to exert guiding pressure on a means to accept pressure of a correspondingly, externally threaded nut, and the correspondingly, externally threaded nut for attachment within the internally threaded wall, which threaded nut has an extension which is perforately slotted, the nut extension having the means to accept pressure, so as to cause it to be directed inwardly by tightening of the nut within the internally threaded wall, so as to cause the snug contact between the lower interior surface of the support member and the exterior cylindrical surface of the stator.

The invention is useful in measuring viscosities with sensitive rotating viscometers, especially Brookfield viscometers.

Significantly, by the present invention, problems of the prior art of Deysarkar et al. are ameliorated or eliminated. The adapter hereof provides for precise centering of the rotor spindle in the stator of a sensitive rotating viscometer. Moreover, the article of the invention is readily made—and is easily and effectively used, to especially include by even inexperienced operators.

Numerous further advantages attend the invention.

DRAWINGS IN BRIEF

The drawings form part of the specification hereof.

In the drawings, in which like numerals refer to like features, note:

FIG. 1 is an exploded cross-sectional view of a rotor-stator adapter with an internally threaded stator collar and externally threaded nut for sensitive rotating viscometers of the invention.

FIG. 2 is a partial cross-sectional view of a stator collar and nut for the rotor-stator adapter such as of the FIG. 1 invention with tapered threads, in assembly with a stator and collar housing.

FIG. 3 is a side view of a nut generally of FIGS. 1 & 2.

FIG. 4 is a top view of a nut such as in FIG. 3.

ILLUSTRATIVE DETAIL

In reference to the drawings, adapter 200 has receiving wall 280 on stator collar 270 which is internally threaded 281. It can be considered to be in a lower portion of the support member assembly, collar housing 140. The receiving wall 280 has means to exert guiding pressure on a means to accept pressure of a correspondingly, externally threaded nut 290, which means to exert pressure can be a protrusion such as a shoulder or bevel 284 near the interior terminus of the internal threads 281 or such as tapered threads 285.

The nut 290 has external threads 291 corresponding to the internal threads 281 of the receiving wall 280 for attachment thereof within the internally threaded wall 280. The threaded nut 290 has extension 299 which is perforately slotted 292 to provide fingers 293, which can bend inwardly upon exertion of a suitable pressure from the means to exert guiding pressure of the receiving wall 280. The nut extension 299 has the means to accept pressure, so as to cause it to be directed inwardly by tightening of the nut within the internally threaded wall, which means to accept pressure can be another protrusion such as a ramp or reverse bevel 294 near the distal terminus of the external threads 291 or such as tapered threads 295. Such pressure-receiving other protrusion may be provided by a first, upper thread from among threads 291.

In practice, the threaded parts, i.e., stator collar 270 and nut 290, are screwed together to a suitable torque. This causes the snug contact between the lower interior surface of the support member, in practice, this surface 254 being on the inside of the nut 290 thus, and the exterior cylindrical surface of the stator 28. The cylindrical lower assembly interior surface 254 is dimensioned to receive and encircle an upper end of the stator 28.

Perfect centering of a Brookfield viscometer rotor 30 (suspended from a pivot of pivot housing 20 of viscometer head 10) within the stator 28 about axis of rotation 122 is achieved by simply slipping the stator through the upper end of the stator collar 270 until stator annular lip 56 contacts upwardly-directed stop surface 258, which is followed by the tightening of the nut 290, and insertion of the stator, nut and collar assembly into a suitable collar housing 140.

Pin 177 of the collar housing 140 may provide vertical fastening of the collar housing 140 to the stator collar 270. The pin, which may be, for example, a spring plunger, may rest in plunger hole 286 of the stator collar, first riding up ramp 287 as the stator collar, nut and stator assembly is inserted into the collar housing 140.

Plate 143 may be present with the collar housing 140. Leveling of the plate is easily and reliably accomplished as is well-known in the art.

The adapter may be made of any suitable material. Advantageously, it is made of a thermally-insulating engineering material to include engineering thermoset resins and engineering thermoplastics such as homo- or co-polymeric acetal resins, which may be injection molded and/or machined to the required dimensions and tolerances. For instance, DELRIN acetal homopolymer (The Polymer Corp., Reading, Pa.) may be thus employed to produce adapter components hereof.

CONCLUSION

The present invention is thus provided. Numerous modifications can be effected by those skilled in the art in the spirit of the invention, the distinctiveness of which is particularly pointed out as follows:

I claim:

1. In a device for supporting a sensitive rotating viscometer above a stator having a cylindrical tube for containing a predetermined quantity of fluid, the fluid having a viscosity, the viscosity of the fluid being measured by a viscometer with a motor, and with a cylindrical rotor suspended from a pivot housing fixed to a lower end of the viscometer and centered within the fluid by the device, the rotor being rotatable about its longitudinal axis by the motor of the viscometer and cooperating with the stator and fluid to create drag related to the viscosity, the device having a hollow support member having an open upper end and upper interior surface shaped to correspond and snugly engage an exterior surface of the pivot housing, the viscometer projecting upwardly from substantially an upper end of the support member, first means for retaining the pivot housing in stationary position and snug contact with the upper interior surface of the hollow support member, the support member further including a lower interior cylindrical surface in snug contact with an exterior cylindrical surface of the stator, and second means for retaining the stator in stationary position and snug contact with the lower cylindrical surface of the hollow support member, the upper and lower surfaces being coaxial with each other to substantially precisely center the axis of the cylindrical rotor within the stator so as to help provide sensitivity and accuracy in the sensitive rotating viscometer by permitting thin layers of fluid to be tested for viscosity, an improvement which comprises:

an internally threaded wall in a lower portion of the hollow support member, having means to exert guiding pressure on a means to accept pressure of a correspondingly, externally threaded nut, and the correspondingly, externally threaded nut for attachment within the internally threaded wall, which threaded nut has an extension which is perforately slotted, the nut extension having the means to accept pressure, so as to cause the nut extension to be directed inwardly by tightening of the nut within the internally threaded wall, so as to cause the snug contact between the lower interior surface of the hollow support member and the exterior cylindrical surface of the stator.

2. The improvement of claim 1, wherein the hollow support member includes collar housing, and the internally threaded wall is on a stator collar, which can be snugly fitted into the collar housing of the hollow support member for supporting the viscometer.

3. The improvement of claim 2, wherein the means to exert guiding pressure is provided by a bevel disposed about the top of the threads of the internally threaded wall, and the means to accept the pressure therefrom is provided by a corresponding reverse bevel placed about the top of the externally threaded nut.

4. The improvement of claim 2, wherein the means to exert guiding pressure is provided by tapered threads placed on the internally threaded wall, and the means to accept the pressure therefrom is provided by a corresponding set of tapered threads placed on the externally threaded nut.

5. An article of manufacture having a tube collar supported by and fastened into a hollow collar housing in a cylindrical axially-aligned manner by means of complementary mating threads useful for securing a stator tube, said article comprising a hollow collar housing having a cylindrical inside wall; a tube collar having a cylindrical outside wall which can be snugly fitted into the hollow collar housing about a lower portion of the hollow collar housing, where said tube collar is to be mated with an externally threaded nut designed to mate with said tube collar by joining on a connecting portion of the tube collar; where the tube collar also has an internally threaded wall having means to exert guiding pressure on a means to accept pressure of the correspondingly, externally threaded nut; where the correspondingly, externally threaded nut, is for attachment within the internally-threaded wall the correspondingly, externally threaded nut for attachment within the internally threaded wall, which threaded nut has an extension which is perforately slotted to provide fingers, that serve to secure said stator tube the nut extension having the means to accept pressure, so as to cause the fingers of the nut extension to be directed inwardly by tightening of the nut within the internally threaded wall, so as to cause snug contact between the fingers of the nut extension and an exterior surface of the stator tube as held centrally within said fingers.

6. The article of claim 5, wherein the hollow collar housing has a plate extending outwardly therefrom.

7. The article of claim 6, wherein vertical fastening of the hollow collar housing to the tube collar is provided.

8. The article of claim 7, wherein the vertical fastening is provided by a pin which rests in a receiving hole of the tube collar.

9. The article of claim 8, wherein the pin is a spring plunger.

10. The article of claim 9, wherein a ramp is provided on the outside of the tube collar above the receiving hole of the tube collar so that the spring plunger can ride up the ramp and spring into the hole of the tube collar when the tube collar is inserted into the hollow collar housing.

11. An article of manufacture useful for mating with a hollow collar housing having a cylindrical inside wall, with said article further useful for securing a stator tube thereto; said article comprising a tube collar having a cylindrical outside wall and an internally-threaded wall where said tube collar is to be mated with an externally-threaded nut designed to mate with said tube collar by joining on a connecting portion of the tube collar; said internally-threaded wall having means to exert guiding pressure on a means to accept pressure of the correspondingly externally-threaded nut, where the externally-threaded nut is disposed for tight mechanical attachment within the internally-threaded wall, the correspondingly, externally-threaded nut being axially-aligned for mated thread attachment within the internally-threaded wall, which externally-threaded nut has an extension which is perforately-slotted to provide a set of fingers that serve to secure the said stator tube, said threaded nut extension having the means to accept pressure, so as to cause the fingers of the threaded nut extension to be directed inwardly by tightening of the nut within the internally-threaded wall, thereby causing snug contact between the fingers of the nut extension and an exterior surface of the stator tube as held centrally within said set of fingers.

\* \* \* \* \*